United States Patent [19]

Gray et al.

[11] Patent Number: 5,517,181
[45] Date of Patent: May 14, 1996

[54] HAZARDOUS FLUID LEAK DETECTOR

[75] Inventors: Harold E. Gray; Felder M. McLaurin; Monico Ortiz; William A. Huth, all of Las Vegas, Nev.

[73] Assignee: The United States of America as represented by the United Staes Department of Energy, Washington, D.C.

[21] Appl. No.: 289,342

[22] Filed: Aug. 10, 1994

Related U.S. Application Data

[63] Continuation of Ser. No. 73,375, Jun. 8, 1993, abandoned.

[51] Int. Cl.$^6$ .................................................. G08B 21/00
[52] U.S. Cl. ...................... 340/605; 324/449; 324/450; 204/416; 204/417
[58] Field of Search ........................... 340/605; 324/449, 324/450; 204/416, 417

[56] References Cited

U.S. PATENT DOCUMENTS

| | | | |
|---|---|---|---|
| 1,320,036 | 10/1919 | Crockatt | 324/450 |
| 2,156,693 | 5/1939 | Jacobson | 23/232 |
| 2,795,756 | 6/1957 | Jacobson et al. | 324/30 |
| 2,934,408 | 4/1960 | Brooke | 23/232 |
| 2,939,827 | 6/1960 | Jacobson et al. | 204/195 |
| 3,040,245 | 6/1962 | Brizzolara | 324/30 |
| 4,228,400 | 10/1980 | Bruckenstein et al. | 324/449 |
| 4,326,200 | 4/1982 | Bushman | 340/632 |
| 4,478,704 | 10/1984 | Miyoshi et al. | 204/412 |
| 4,513,280 | 4/1985 | Hannan et al. | 340/632 |
| 5,137,608 | 8/1992 | Acar et al. | 204/130 |

*Primary Examiner*—John K. Peng
*Assistant Examiner*—Edward Lefkowitz
*Attorney, Agent, or Firm*—Miguel A. Valdes; William C. Daubenspeck; William R. Moser

[57] ABSTRACT

A device or system for monitoring for the presence of leaks from a hazardous fluid is disclosed which uses two electrodes immersed in deionized water. A gas is passed through an enclosed space in which a hazardous fluid is contained. Any fumes, vapors, etc. escaping from the containment of the hazardous fluid in the enclosed space are entrained in the gas passing through the enclosed space and transported to a closed vessel containing deionized water and two electrodes partially immersed in the deionized water. The electrodes are connected in series with a power source and a signal, whereby when a sufficient number of ions enter the water from the gas being bubbled through it (indicative of a leak), the water will begin to conduct, thereby allowing current to flow through the water from one electrode to the other electrode to complete the circuit and activate the signal.

5 Claims, 2 Drawing Sheets

HAZARDOUS FLUID LEAK DETECTOR

This is a continuation of application Ser. No. 08/073,375, filed Jun. 8, 1993, now abandoned.

BACKGROUND OF THE INVENTION

The invention described herein arose in the course of, or under, Contract No. DE-AC08-88NV10617 between the United States Department of Energy and EG&G Energy Measurements, Inc.

This invention relates to a hazardous fluid leak detector apparatus. More particularly, this invention relates to an apparatus which will detect the presence of hazardous fluids by passing a gas from a monitored enclosure through a body of deionized water containing electrodes in series with a power source and an alarm. Any fumes, vapors, or liquids of hazardous fluids, entrained in the gas which enters the deionized water, will cause the water to conduct, to thereby activate the alarm.

In the prior art, testing and monitoring for the presence of certain gases or liquids has been carried out by passing a gas through a liquid in a vessel containing electrodes. These electrodes are then connected to measuring devices which respectively measure voltage generated by the electrodes, or the pH of the liquid, or changes in resistance between the electrodes. Such detection systems are then, in turn, usually connected to visual or audible devices which signal changes in the gas content passing into the liquid.

For example, the monitoring of voltage generation, or voltage changes between electrodes immersed in a liquid through which a gas is passed, is described in Jacobson U.S. Pat. No. 2,156,693; Jacobson et al. U.S. Pat. Nos. 2,795,756 and 2,939,827; Bushman U.S. Pat. No. 4,326,200; and Miyoshi et al. U.S. Pat. No. 4,478,704.

Jacobson U.S. Pat. No. 2,156,693 describes a structure for testing for the presence of a gas using an electrode which is reactive with the gas to be detected. The electrode which is reactive with the gas is partially immersed in an electrolyte such as ammonium hydroxide or ammonium chloride. A second electrode is totally immersed in the electrolyte. When the partially immersed electrode is contacted by the gas to be detected, the reaction between the gas and the electrode causes an EMF to be generated between the two electrodes. The EMF so generated is then measured by means such as a milliammeter and a Wheatstone bridge to determine the concentration of the gas.

Jacobson et al., U.S. Pat. No. 2,795,756 discloses an elaborate electrical control system used to process the signal from a galvanic cell which is used to measure the concentration of gases which pass through the cell.

Jacobson et at. U.S. Pat. No. 2,939,827 describes a Fery type primary galvanic cell used to determine the oxygen content of a gas using a zinc anode, a porous carbon electrode, and an ammonium chloride electrolyte in which depolarization of the cathode depends upon the diffusion of oxygen in the sample mixture through the cathode to the electrode-electrolyte interface, where it oxidizes the hydrogen ions there liberated. The measured electrical energy of the cell is a function of the oxygen concentration in the sample.

Bushman U.S. Pat. No. 4,326,200 describes a device for detecting $CO_2$ comprising a vessel containing water wherein a layer of ion-exchange resin wetted by the water is sandwiched between air and water-permeable electrode gauze discs. Any $CO_2$ gas in the ambient atmosphere dissolves in the water and the dissociated ions lower the resistance between the electrodes. The electrodes may be connected to a bridge circuit adjusted to be out of balance at a predetermined $CO_2$ level; or the electrodes may be formed of dissimilar metals to form a galvanic cell with a measurable output current at a predetermined $CO_2$ concentration.

Miyoshi et al. U.S. Pat. No. 4,478,704 shows a gas detection device for detecting levels of CO and $H_2$ using an electrolytic cell containing a working electrode, a reference electrode, and a counter electrode, with a sulfuric or phosphoric acid electrolyte. Voltages changes between the electrodes, indicative of changes in the levels of CO and $H_2$ passing through the cell, are monitored.

Brooke U.S. Pat. No. 2,934,408 and Hannan et at. U.S. Pat. No. 4,513,280 monitor pH changes in a liquid caused by passing a gas through the liquid. The Brooke patent teaches apparatus for detecting the presence of acetylene in ethylene by passing the ethylene gas through a vessel containing silver nitrate and a buffering agent. Any acetylene in the gas reacts with the silver nitrate to form nitric acid. After the buffering agent is expended, the nitric acid causes the pH to drop. Electrodes in the vessel connected to a pH meter record the drop in pH which activates a valve to shut off the gas flow. A flowmeter records the amount of gas passed into the cell prior to this shut off to permit determination of the concentration of the acetylene in the ethylene gas.

In the Hannan et al. patent, cells are disclosed for detecting $CO_2$ levels in water based on a reduction in pH in the water. The $CO_2$ enters the chamber in which the ph is being monitored through a $CO_2$ permeable membrane.

The above-mentioned Bushman patent also discloses the measurement and monitoring of resistance changes in the liquid, as is also taught in Brizzolara U.S. Pat. No. 3,040,245. In the Brizzolara patent, there is disclosed a gas detector wherein gases from several locations are pumped through tap water in a flask which also contains electrodes. The electrodes are immersed in the tap water and electrically connected to a resistance measuring unit which monitors the changes in conductivity of the water. The resistance monitoring unit, in turn, controls a power supply and a signal. The signal is thereby activated when the gas supplied into the water causes a predetermined change in the conductivity or resistivity of the water.

What all of the above described systems or devices, however, share in common is a detection system, which then, in turn, is coupled to some sort of visual or audible monitoring device or signal. The disclosed detection systems are usually somewhat elaborate and complicated, for example, requiting bridges for measuring small voltages or changes in resistance, etc. In the case of Brizzolara, for example, the electrodes immersed in the liquid to monitor the resistance changes in the liquid, are connected to the grid of an triode vacuum tube, as well as to a grid power supply (C voltage), with the plate of the vacuum tube connected to a B+ voltage and a relay. The contacts of the relay are, in turn, then connected in series with yet another power supply and a signal.

It would, therefore, be desirable to provide a much simpler monitoring device which would require no separate detection system or circuitry, but which could rather be connected directly to a power supply and alarm signal and wherein the liquid used to monitor the presence of gas could be easily replenished, without any need for the recalibration of measuring devices used with the liquid.

SUMMARY OF THE INVENTION

The invention comprises a device or system for monitoring for the presence of leaks from a hazardous fluid in an enclosed space by passing a gas through the enclosed space and then through a closed vessel containing deionized water and two electrodes partially immersed in the aleionized water. The electrodes are connected in series with a power source and a signal, whereby when a sufficient number of ions enter the water from the fluid being passed through it (indicative of a leak), the water will begin to conduct, thereby allowing current to flow through the water from one electrode to the other electrode to complete the circuit and activate the signal.

DETAILED DESCRIPTION OF THE INVENTION

Figure 1:
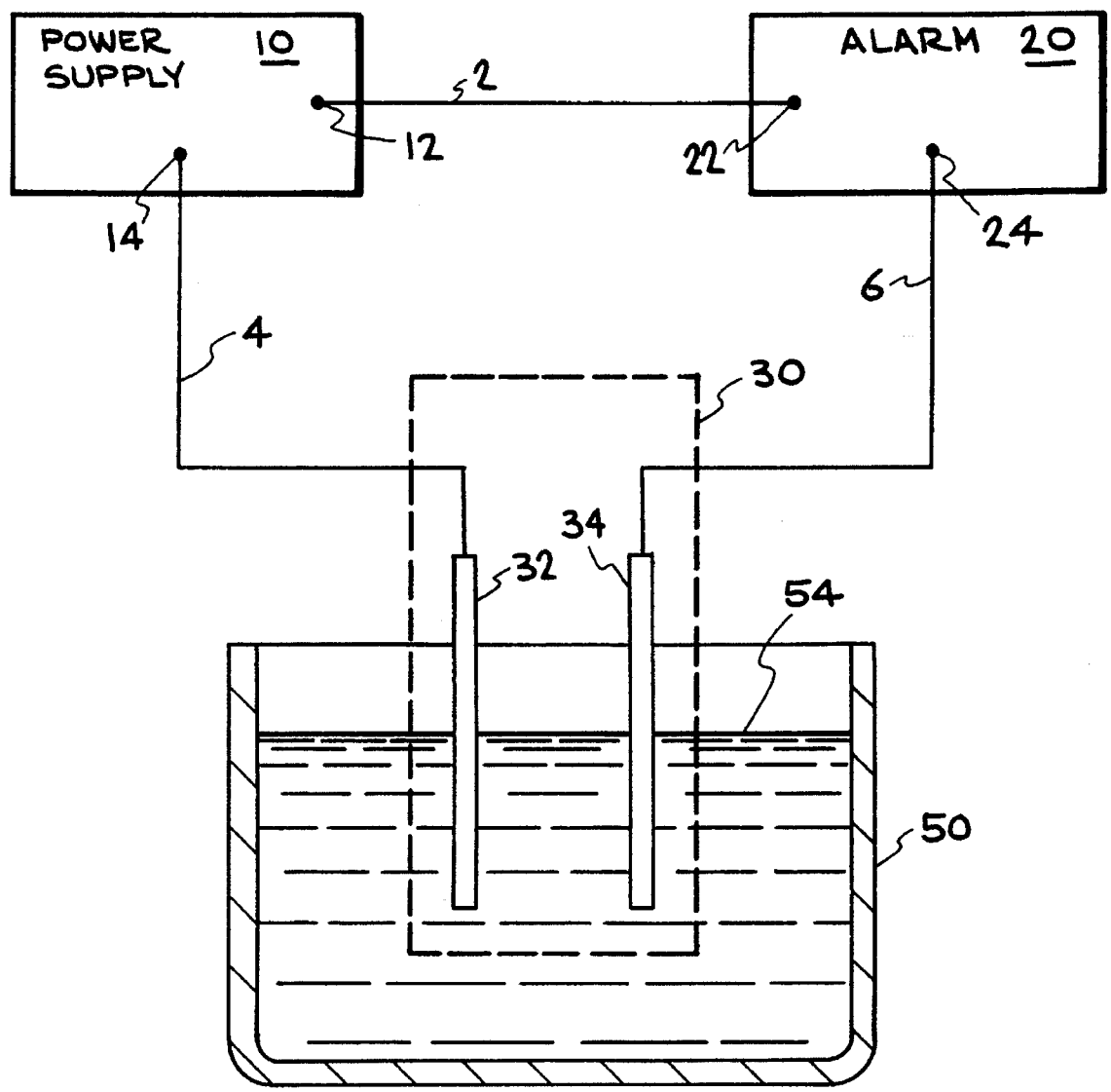
FIG. 1 schematically illustrates the electrical circuit of the monitoring system.

The invention provides a device or system for monitoring for leaks of a hazardous fluid in an enclosed space, which utilizes the very high resistance of deionized water to permit electrodes immersed in the water, and electrically connected in series with a power supply and an alarm, to function as a simple 'switch' which prevents the alarm from being activated by the power supply unless the 'switch' is turned on.

The term "deionized water", as used herein, is intended to defme a purified form of water having a conductivity of 1 microSiemen/cm or less. Such a low conductivity is in marked contrast, for example, to water with as little as 0.01 grams of KCl dissolved therein resulting in a conductivity of 1409 microSiemens/era, or 31% nitric acid having a conductivity of 865,000 microSiemens/cm.

In accordance with the invention, a gas such as nitrogen is circulated through an enclosed volume containing storage containers having hazardous fluids or like therein, and any fumes, vapors, aerosols, etc, representing leakage of such hazardous fluids from the containers in the enclosed space, is entrained in the circulating gas. This circulating gas is then introduced into a vessel containing aleionized water at a point below the water level. Immersed in the fieionized water are two electrodes which are connected in series with a power supply and an alarm. If the circulating gas contains ions from any such fumes, aerosols, or vapors entrained in the circulating gas, these ions will pass into the aleionized water, thereby causing the water to conduct, which completes the circuit between the alarm and the power supply, i.e., tums the "switch" on.

The gas used for this purpose should not, in and of itself, contribute any ions to the deionized water through which it is being passed, so that any ions entering the deionized water will be solely attributable to the hazardous fluids which have become entrained in the gas. Gases which meet this criteria include, for example, rare gases such as argon, xenon, and helium or non-reactive gases such as nitrogen.

In this regard, it should be noted that the actual amount of current which flows through the circuit will also be dependent upon the voltage of the power supply and the geometry of the "switch", i.e., the area of the electrodes, the spacing apart of the electrodes, and the extent of immersion of the electrodes.

Also the range of use of the device, i.e., the hazardous fluids to which any given device will be sensitive, will be dependent upon the influence of the particular fluid on the conductivity of the deionized water. That is, the sensitivity of the device to a particular fluid depends upon how much that particular fluid will change the conductivity of the aleionized water. For example, the resistance per gram of chemical in 100 grams of water for acetic acid (in low concentrations) is 65 ohms/cc, while for hydrochloric acid, the resistance per gram of HCl in 100 grams of water (in similar concentrations) is about 0.1 ohms/co.

Generally speaking, for any given geometry of the "switch", i.e., electrode area, spacing, degree of immersion, etc., the resistance of the alarm should be very low relative to the resistance of the "switch" in deionized water, so that substantially all of the voltage will be dropped across the "switch", rather than across the alarm when no ions are being deposited in the water by the gas circulating through the hazardous fluids storage area, i.e., when no leaks to detect are occurring. By use of the term "very low" is meant that the resistance of the alarm should be within a range of from about 0.1% to about 0.0001% of the resistance of the "switch" in deionized water. leak detector apparatus of the invention may be operated over a wide range of temperatures, but preferably should be operated at temperatures above about 0° C.

Turning now to FIG. 1, the operation of the electrical circuit and the "switch" is shown wherein a power supply 10 has one terminal 12 connected via a conductor 2 to a terminal 22 on an alarm 20, and another terminal 14 connected by conductor 4 to first electrode 32 of switch 30. Another terminal 24 on alarm 20 is connected, via conductor 6, to a second electrode 34 in switch 30 which is spaced from first electrode 32. Both electrodes 32 and 34 are shown spaced apart in a vessel 50 capable of holding a liquid. When sufficient deionized water 54 is placed in vessel 50 to at least partially immerse electrodes 32 and 34 therein, an insufficient mount of current will flow in the circuit defined by power supply 10, alarm 20, conductors 2, 4, and 6, and the gap between electrodes 32 and 34 to activate alarm 20. This is because the substantial absence of ions in the deionized water in the gap between electrodes 32 and 34 results in substantially no current flow. "Switch" 30 thus remains in an "off" state.

However, when a gas containing fumes, vapors or aerosols of, for example, leaking hazardous fluids is passed through the deionized water, ions from such entrained fumes, vapors, or aerosols pass into the deionized water, allowing ion/electron flow through the water between electrodes 32 and 34, i.e., closing the gap or "switch", thereby completing the circuit to allow current to flow to alarm 20 from power supply 10.

Figure 2:
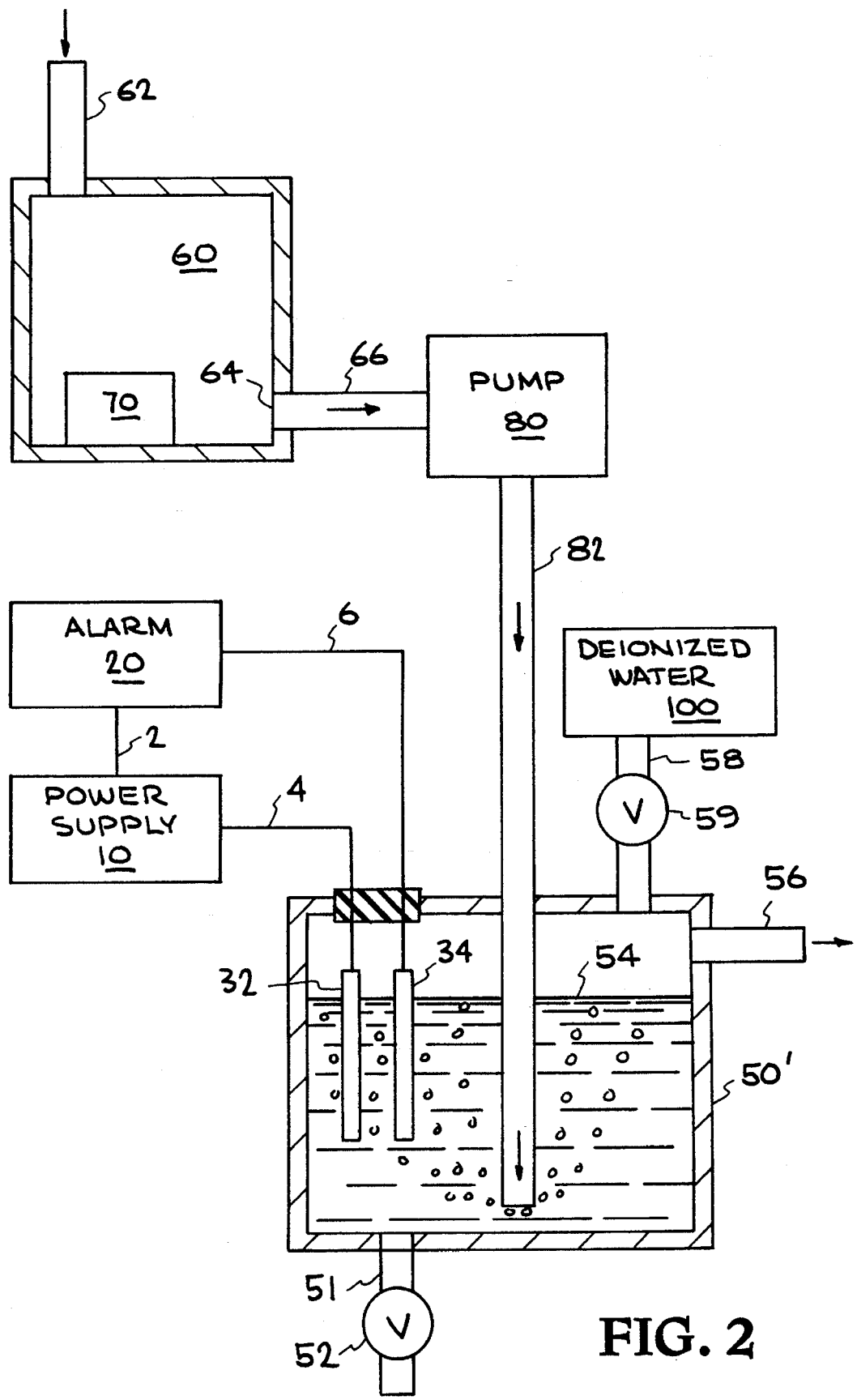
FIG. 2 schematically illustrates the physical relationship of the components of the monitoring system.

Turning now to FIG. 2, there is depicted that portion of the system which couples an enclosure 60, where the hazardous fluid to be monitored is stored, to "switch" 30 of FIG. 1. As shown in FIG. 2, enclosure 60 confines a hazardous fluid source 70, which might comprise a container, valve, fitting, pump, etc. When source 70 is a container or a pump, for example, enclosure 60 might be a rigid enclosure, while a valve or a fitting might be enclosed by a more flexible enclosure 60 such as, for example, a plastic bag.

In any event, enclosure 60 is provided with an ingress port 62 through which air, or a gas of known purity (and ion content) such as nitrogen, argon, helium, etc., may be allowed to pass into enclosure 60. The gas passing through enclosure 60 then exits via exit port 64 and passes through conduit 66 to pump 80 which, in turn, then pumps the gas through conduit 82 into an enclosed vessel 50' which is at least partially filled with aleionized water 54.

As shown in FIG. 2, conduit 82 preferably terminates adjacent the bottom of vessel 50', so that the gas exiting conduit 82 will travel upwardly through the bulk of liquid 54 before arriving at the surface, where it then passes out of vessel 50' via exit port 56.

As previously discussed, when the gas passing through enclosure 60 encounters vapors, fumes, etc. from toxic gases or liquids escaping from container 70, such fumes or vapors are entrained in the circulating gas and are then introduced into deionized water 54 in vessel 50' as the gas leaves conduit 82 and bubbles through vessel 50'. The ions from these entrained fumes or vapors enter aleionized water 54 causing it to become conductive to permit current to flow between electrodes 32 and 34 immersed in aleionized water 54, which in turn completes the circuit allowing power supply 10 to activate alarm 20.

Since the alarm system merely uses aleionized water, once the leak is corrected, the system is very easily reactivated by draining out the contaminated deionized water, using drain 51 and valve 52, and fresh deionized water is then admitted to closed vessel 50' via conduit 58 and valve 59 from deionized water source 100. Since the system relies on merely the deionized water either conducting or not conducting, depending upon whether or not fumes or vapors are entrained in the gas being bubbled through the water, there is no need to recalibrate anything in order to restart or reset the system.

It should be pointed out that since the detection system works on the basis of introducing ions into the aleionized water to render it conductive, the detection system may be used with either basic or acidic materials.

It should be noted that in the system just described, neither tap water nor demineralized water possess a sufficiently low conductivity to be operative. That is, a sufficient current from the power supply would pass through the water between the electrodes to activate the alarm without any gas flow through the water. This is why prior art systems devised circuitry to compare the relative flows of current, as opposed to the simplicity of operation of the herein described invention. Thus, it is important to the practice of the invention that deionized water always be used.

Alarm 20, in its simplest form, may merely comprise a visual signal, such as a light; or an audible signal such as a buzzer or a bell. Alternatively, alarm 20 may comprise, for example, the input to a microprocessor wherein, in response to the input signal, one or more appropriate responses may be initiated, such as shutdown of systems, opening or closing of valves, notifications to personnel, etc.

To illustrate the practice of the invention, electrode plates, having a conducting surface area of 1 cm$^2$, with the rear surfaces of the plates insulated, may be immersed in aleionized water at a spacing of 1 cm. apart. The electrodes are connected in series with a power supply and an alarm having a resistance of about 2 k$\Omega$. A potential of 1 volt applied by the power supply, gives rise to a current flow across the electrodes of 0.5 microamps, which is insufficient to activate the alarm. Less than 1 gram/liter of hydrochloric acid then added to the water, results in an increase in current flowing across the electrodes up to 500 microamps, a 1000 fold increase, which is sufficient to activate the alarm.

Thus, the invention provides a simplified, but very sensitive, hazardous fluid leak detector apparatus which does not require complicated monitoring systems to measure and compare either generated voltages, or changes in pH or resistivity, and therefore does not require recalibration of such systems each time the detector system is used and then reactivated or reset. The system is also relatively inexpensive and may be easily duplicated for simultaneous monitoring of a number of potential sources of leaks using, for example, the same power supply and alarm components with a plurality of electrode/deionized water subsystems placed in parallel across the series-connected power supply and alarm components. While a specific embodiment of the hazardous fluid leak detection system of the invention has been illustrated and described for operating the leak detection system in accordance with this invention, modifications and changes of the apparatus, parameters, materials, etc. will become apparent to those skilled in the art, and it is intended to cover in the appended claims all such modifications and changes which come within the scope of the invention.

What is claimed is:

1. An apparatus for detecting leaks of a hazardous material from an enclosure, said material being confined in said enclosure, while confining said leaks of hazardous material in an enclosed space which comprises:

means for containing said leaks of said hazardous material from said enclosure in an enclosed space;

a vessel containing an electrically non-conductive liquid;

a source of a reference gas, said reference gas being of a type that does not contribute ions when said gas is absorbed in said electrically non-conductive liquid;

means for supplying said reference gas from said source of a reference gas to said enclosed space and circulating said reference gas through said enclosed space for entraining at least part of said leaked hazardous material in said circulating reference gas;

means for extracting said circulating reference gas from said enclosed space and transporting said extracted reference gas into said non-conductive liquid contained in said vessel; and means for detecting changes in the conductivity of said non-conductive liquid resulting from ions of said leaked hazardous material deposited in said non-conductive liquid by said extracted reference gas.

2. The leak detection apparatus of claim 3 further comprising:

means for draining said non-conductive liquid from said vessel; and means for replenishing said non-conductive liquid in said vessel.

3. The leak detection apparatus of claim 2 wherein said means for detecting conductivity changes in said non-conductive liquid further comprises an alarm to signal when the conductivity of said non-conductive liquid has changed by a predetermined amount.

4. The leak detection apparatus of claim 1 wherein said hazardous material is a liquid.

5. The leak detection apparatus of claim 1 wherein said non-conductive liquid is deionized water.

\* \* \* \* \*